US007381828B2

(12) United States Patent
Larsson et al.

(10) Patent No.: US 7,381,828 B2
(45) Date of Patent: Jun. 3, 2008

(54) TRIAZOLO PYRIMIDINE COMPOUNDS

(75) Inventors: Ulf Larsson, Södertälje (SE); Mattias Magnusson, Södertälje (SE); Tibor Musil, Södertälje (SE); Andreas Palmgren, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 11/591,464

(22) Filed: Nov. 2, 2006

(65) Prior Publication Data

US 2007/0049755 A1 Mar. 1, 2007

Related U.S. Application Data

(63) Continuation of application No. 11/255,838, filed on Oct. 24, 2005, now abandoned, which is a continuation of application No. 10/275,560, filed as application No. PCT/SE01/01241 on May 31, 2001, now Pat. No. 7,067,663.

(30) Foreign Application Priority Data

Jun. 2, 2000 (GB) ................. 0013488.2
Jun. 6, 2000 (SE) ................... 0002102

(51) Int. Cl.
C07D 317/44 (2006.01)
(52) U.S. Cl. .................................... 549/437
(58) Field of Classification Search ................ 549/437
See application file for complete search history.

(56) References Cited

U.S. PATENT DOCUMENTS

| 5,654,285 | A | 8/1997 | Ingall et al. .......... 514/47 |
| 5,905,085 | A | 5/1999 | Borcherding et al. |
| 6,251,910 | B1 | 6/2001 | Guile et al. ......... 514/261.1 |
| 6,525,060 | B1 | 2/2003 | Hardern et al. ..... 514/261.1 |
| 6,713,483 | B1 | 3/2004 | Guile et al. ......... 514/261.1 |
| 6,974,868 | B2 | 12/2005 | Hardern et al. ........ 544/254 |
| 2003/0181469 | A1 | 9/2003 | Bohlin et al. ........ 514/261.1 |

FOREIGN PATENT DOCUMENTS

| EP | 0 508 687 A1 | 10/1992 |
| EP | 0 508 687 B1 | 9/1995 |
| WO | WO 91/01317 | 2/1991 |
| WO | WO 97/03084 | 1/1997 |
| WO | WO 97/03084 A1 | 1/1997 |
| WO | WO 99/05143 | 2/1999 |
| WO | WO 99/41254 | 8/1999 |
| WO | WO 00/34283 | 6/2000 |

OTHER PUBLICATIONS

Marco-Contelles, J., et al; "Synthesis and transformations of (1R, 2R, 3S, 4R)-4-O-benzylhydroxylamino-2,3-O-isopropylidene-1,2,3-cyclopentanetriol:synthesis of (1S,2R,3S,4R)-4-amino-2,3-O-isopropylidene-1,2,3-cyclopentanetriol"; *Tetrahedron: Asymmetry*, vol. 8, No. 13; pp. 2249-2256 (1997).
Chen, J., et al; "A Novel and Efficient Route to Chiral 2-Substituted Carbocyclic 5'-N-Ethyl-Carboxamido-Adenosine (C-NECA)"; *Tetrahewdron Letters*, vol. 30, No. 41, pp. 5543-5546 (1989).
Jung, M., et al; "188. Total Synthesis of Neplanocin A"; *Helv. Chim. Acta*; vol. 66, Fasc. 7, Nr. 188, pp. 1915-1921 (1983).
Jung, M. et al; "188. Total Synthesis of Neplanocin A"; vol. 66, No. 7; pp. 1915-1921 (1983).
Vorozhtsov, "Foundations of intermediate products and colorants synthesis"; *State Scientific Technical Publishing House of Chemical Literature*; Moscow, p. 255 (1955).
Weigand-Hilgetag, "Methods of Experimentation in Organic Chemisrt" (translation of the 3rd German edition); *Publishing House Chemistry*; Moscow, p. 202 (1968).
Helvetica Chimica Acta, 1983, vol. 66, No. 7, pp. 1915-1921.

*Primary Examiner*—Janet L. Andres
*Assistant Examiner*—Raymond Covington
(74) *Attorney, Agent, or Firm*—Nixon & Vanderhye

(57) ABSTRACT

The present invention relates to a pyrimidine compound (I) useful as a pharmaceutical intermediate, to a process for preparing said pyrimidine compound, to intermediates used in said process, and to the use of said pyrimidine compound in the preparation of pharmaceuticals.

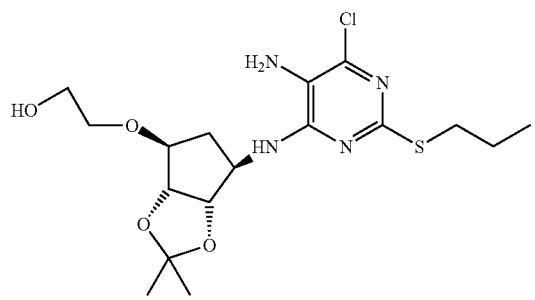

3 Claims, No Drawings

TRIAZOLO PYRIMIDINE COMPOUNDS

This application is a continuation of application Ser. No. 11/255,838, filed Oct. 24, 2005, now abandoned which is a continuation of application Ser. No. 10/275,560, filed Nov. 7, 2002, now U.S. Pat. No. 7,067,663, which is a 371 of PCT/SE01/01241 filed May 31, 2001, the entire content of which is hereby incorporated by reference in this application.

The present invention relates to a pyrimidine compound useful as a pharmaceutical intermediate, to a process for preparing said pyrimidine compound, to intermediates used in said process, and to the use of said pyrimidine compound in the preparation of pharmaceuticals.

The present invention provides a compound of formula (I):

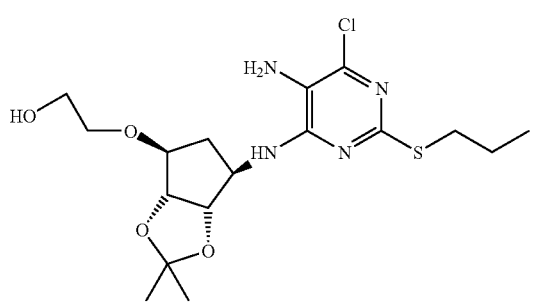

The present invention also provides a process for preparing a compound of formula (I), comprising reacting a compound of formula (II):

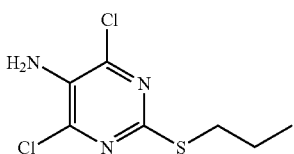

with a salt of a compound of formula (III):

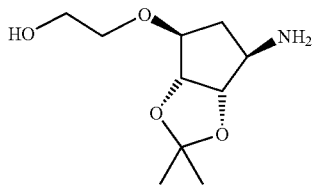

in the presence of a suitable base (such as an alkali metal hydroxide (such as sodium or potassium hydroxide) a tertiary amine (such as a tri($C_{1-6}$ alkyl)amine, for example triethylamine)), a suitable solvent (such as an alcohol, such as an aliphatic alcohol containing from 1 to 6 carbon atoms, for example ethanol), preferably at a temperature in the range 100-150° C. and, cohere necessary (for example when the temperature exceeds the boiling point of the solvent), in a sealed system under autogenic pressure.

A suitable salt of a compound of formula (III) is a salt of a mineral or organic acid. Suitable mineral acids include hydrochloric, hydrobromic, hydroiodic, nitric or sulphuric acid. A suitable organic acid is, for example, an organic achiral acid such as acetic, trifluoroacetic, oxalic or p-toluenesulphonic acid, or an organic chiral acid such as L-tartaric acid, dibenzoyl-L-tartaric acid or di-p-toluoyl-L-tartaric acid.

In another aspect the present invention provides a process for preparing a compound of formula (I) comprising hydrogenating a compound of formula (IV):

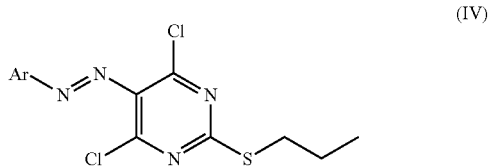

wherein Ar is phenyl optionally substituted by halogen, $C_{1-4}$ alkyl or $C_{1-4}$ alkoxy; to give a compound of formula (II), and reacting the compound of formula (II) with a compound of formula (III) (as described above) to provide the compound of formula (I).

The hydrogenation is preferably conducted using a heavy metal catalyst (such as platinum on carbon), in a suitable solvent (such as a $C_{1-6}$ aliphatic alcohol, for example 2-propanol (iso-propanol)), at a suitable temperature (such as 10-70° C., for example 20-50° C.) and at a suitable pressure (such as 1-5 bar, for example about 3 bar).

A compound of formula (IV) can be prepared by chlorinating a compound of formula (VIII):

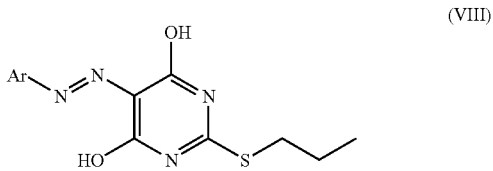

wherein Ar is as defined above, with a suitable chlorinating agent (such as phosphorus oxychloride) in the presence of a suitable nitrogen containing base (such as triethylamine, especially pyridine) and at a suitable temperature (such as in the range 50° C. to the boiling point of phosphorus oxychloride; for example 70 to 90° C.). A compound of formula (VIII) can be prepared by routine adaptation of literature methods.

In a further aspect the present invention provides a process, as hereinbefore described, for the preparation of a compound of formula (II).

The compound of formula (I) can be used to prepare the pharmaceutical compound of formula (A):

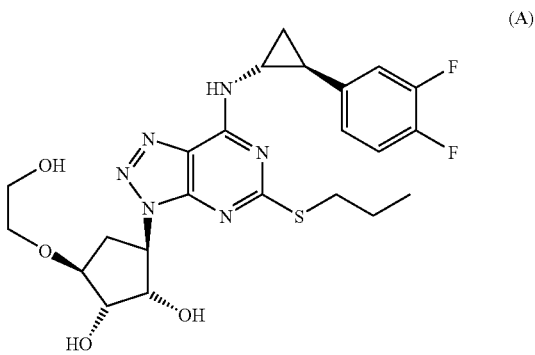

as described below.

Thus, a compound of formula (A) can be prepared by deprotecting a compound of formula (V):

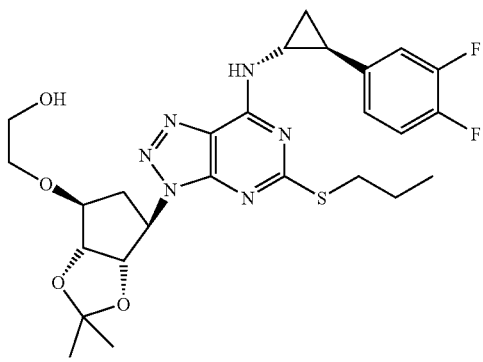

(V)

A compound of formula (V) can be prepared by coupling a compound of formula (VI) {or a salt thereof (such as a mandelate salt) from which the compound of formula (VI) is generated in situ}, with a compound of formula (VII):

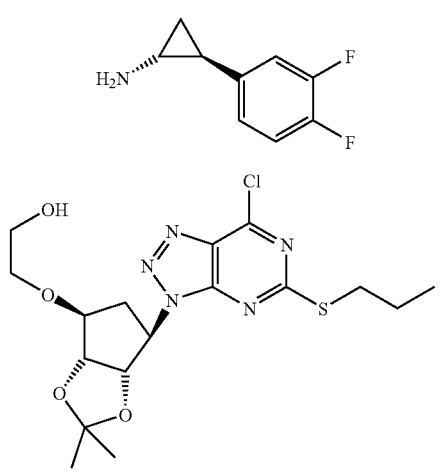

(VI)

(VII)

for example in the presence of a suitable base (such as a tertiary amine, such as a tri($C_{1-6}$ alkyl)amine, for example triethylamine) and a suitable solvent (for example a polar solvent, such as an alcohol (such as an aliphatic alcohol containing from 1 to 6 carbon atoms, for example ethanol) or a nitrile (such as acetonitrile)) and at a suitable temperature (such as a temperature in the range 10-40° C., for example ambient temperature).

A compound of formula M) can be prepared by reacting a compound of formula (I) with an alkali metal nitrite (such as $NaNO_2$) or an organic nitrite (for example iso-amyl nitrite) in the presence of a suitable acid (such as acetic acid) and a suitable solvent (such as water or a mixture of water and acetic acid) and at a suitable temperature (such as a temperature in the range −10 to 15° C., for example −10 to 10° C.).

Thus, in a further aspect the present invention provides the use of the compound of formula (I) in a process for the preparation of the compound of formula (A).

A salt of a compound of formula (III) can be prepared by reacting a compound of formula (III) with the necessary acid in a suitable solvent (such as water, an aliphatic alcohol containing 1 to 4 carbon atoms (for example ethanol) or a simple ester (such as ethyl acetate)) at a suitable temperature (such as from 10 to 60° C., for example 30 to 50° C.).

A compound of formula (III) can be prepared by deprotecting a compound of formula (IX):

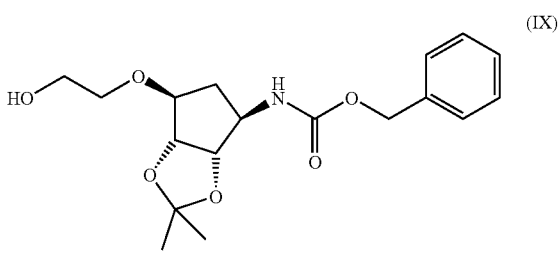

(IX)

for example by hydrogenation {such as with a heavy metal catalyst (such as palladium on carbon) in the presence of a solvent (such as an aliphatic alcohol containing 1 to 4 carbon atoms, for example ethanol) at ambient temperature at a suitable pressure (such as 1 to 3 bar, for example 1.0 to 1.5 bar)}.

A compound of formula (IX) can be prepared by reducing a compound of formula (X):

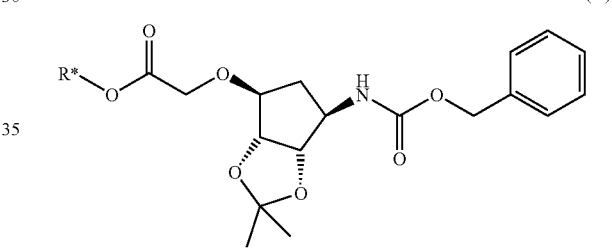

(X)

wherein R* is $C_{1-4}$ alkyl (preferably ethyl), such as with a suitable borohydride (for example an alkali metal borohydride, such as lithium borohydride), lithium aluminiumhydride or DIBAL-H in a suitable polar solvent (such as tetrahydrofuran).

A compound of formula (X) can be prepared by reacting a compound of formula (XI):

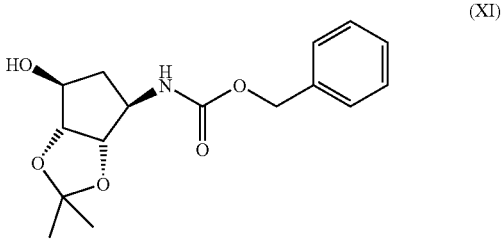

(XI)

with a suitable compound L-$CH_2CO_2R*$ {wherein R* is $C_{1-4}$ alkyl (especially ethyl); and L is a leaving group, especially halogen (for example bromo)}, in the presence of a suitable polar solvent (such as tetrahydrofuran) and in the presence of a suitable base (such as potassium tert-butoxide, sodium hydride or a $C_{1-6}$ alkyl lithium species).

A compound of formula (XI) can be prepared by reacting a compound of formula (XII):

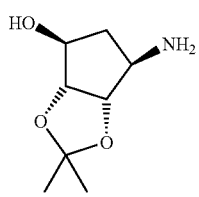

(XII)

with benzyl chloroformate in the presence of a suitable base (such as potassium carbonate) and a suitable solvent (such as a ketone (for example 4-methyl-2-pentanone) or a hydrocarbon (for example toluene)).

In a still further aspect the present invention provides a process for the preparation of a salt of a compound of formula (III) as hereinbefore described.

In further aspects the present invention provides an intermediate compound of formulae (II), (IV), (VII), (VIII), (X) or (XI), or a salt of a compound of formula (III).

The following Examples illustrate the invention.

EXAMPLE 1

This Example illustrates the preparation of 2-{[(3aR,4S, 6R,6aS)-6-amino-2,2-dimethyltetrahydro-3aH-cyclopenta [d][1,3]-dioxol-4-yl]oxy}-1-ethanol, L-tartaric acid salt (1:1).

Step a: Preparation of [3aS-(3aα, 4α,6α,6aα)]-[tetrahydro-6-hydroxy-2,2-dimethyl-4H-cyclopenta-1,3-dioxol-4-yl]-carbamic Acid phenylmethyl ester.

Potassium carbonate (39.3 g) was added to a suspension of [3aR-(3aα,4α,6α,6aα)]-6-amino-tetrahydro-2,2-dimethyl-4H-cyclopenta-1,3-dioxol, hydrochloride, (prepared as described in WO 9905142) (27.1 g) in 4-methyl-2-pentanone (500 ml). Water (150 ml) was then added followed by dropwise addition of benzyl chloroformate (23.1 g). The reaction mixture was stirred at room temperature for 4 hours before the organic phase was separated. The aqueous phase was extracted with 4-methyl-2-pentanone (2×50 ml). The combined organics were concentrated and the residue was purified (SiO$_2$, dichloromethane:methanol, 95:5 to 90:10 as eluant) to give the subtitle compound (39.23 g).

$^1$H NMR (CDCl$_3$) δ 7.32 (5H, m), 5.65 (1H, br s), 5.10 (2H, br s), 4.59 (1H, d), 4.48 (1H, d), 4.27 (1H, m), 4.19 (1H, br m), 2.24 (1H, br s), 1.69 (1H, d), 1.41 (3H, s), 1.26 (3H, s).

Step b: Preparation of [3aS-(3aα,4α,6α,6aα)]-[2,2-dimethyl-6-(2-hydroxyethoxy) -tetrahydro-4H-cyclopenta-1,3-dioxol-4-yl]-carbamic Acid, Phenylmethyl Ester Potassium tert-butoxide (3.6 g) in tetrahydrofuran (20 ml) was added over 5 minutes to a solution of the product from Step (a)(39.23 g) in tetrahydrofuran (200 ml). After 15 minutes, ethyl bromoacetate (3.7 ml) in tetrahydrofuran (10 ml) was added dropwise. The mixture was stirred at 0° C. for 10 minutes, then further ethyl bromoacetate was added (3.7 ml×4). The reaction mixture was stirred at 0° C. a further 2 hours.

Lithium borohydride (2.79 g) was then added portionwise to the reaction mixture which was then stirred at <5° C. for 16 hours. Glacial acetic acid (23 g) was added dropwise to the cold mixture. After stirring for 30 minutes, water (10 ml) was added dropwise and the resulting mixture was stirred for 30 minutes. The phases were then separated and the aqueous phase was extracted with ethyl acetate. The combined organics were washed with saturated sodium bicarbonate and brine, dried and concentrated. The residue was purified (SiO$_2$, ethyl acetate:hexane, 25:75 to 50:50 as eluant) to give the subtitle compound (38.6 g).

MS (APCI) 218 (M+H$^+$, 100%).

Step c: Preparation of [3aR-(3aα,4α,6α,6aα)]-2-[[6-amino-2,2-dimethyl-tetrahydro-4H-cyclopenta-1, 3-dioxol-4-yl]oxy]-ethanol (Alternatively Named: 2-{[(3aR,4S,6R,6aS)-6-amino-2,2-dimethyltetrahydro-3aH-cyclopenta[d][1,3]-dioxol-4-yl]oxy}-1-ethanol)

A slurry of 5% palladium on charcoal (4 g) in ethanol was added to a solution of the product from Step (b) (39.96 g) in ethanol (250 ml) and the mixture was hydrogenated at 1.2 (bar for 20 hours. The catalyst was filtered off and the filtrate was concentrated to give the subtitle compound (23.65 g).

MS (APCI) 160 (M+H$^+$, 100%).

Step d: Preparation of [3aR-(3aα,4α,6α,6aα)]-2-[[6-amino-2,2-dimethyl-tetrahydro-4H-cyclopenta-1, 3-dioxol-4-yl]oxy]-ethanol L tartrate (Alternatively Named: 2-{[(3aR,4S,6R,6aS)-6-amino-2,2-dimethyltetrahydro-3aH-cyclopenta[d][1,3]-dioxol-4-yl] oxy}-1-ethanol, L-tartaric Acid Salt (1:1))

A stirred solution of the product obtained in Step (c) (545 g) in ethanol (3.81) was heated to 35° C. L-tartaric acid (352 g) was added (temperature rise to 45° C.) and the mixture was stirred at 40-45° C. for 1 h. The mixture was cooled to 20° C. and the resulting thick slurry stirred for 16 h then filtered. The collected solid was washed with two portions of 2-propanol (300 ml, then 500 ml), sucked dry then dried in vacuo at 40° C. to give the product as white crystals (728 g).

EXAMPLE 2

This Example illustrates the preparation of trans-(1R,2S)-2-(3,4-difluorophenyl)-cyclopropylamine, R-mandelate salt (alternatively named trans-(1R,2S)-2-(3,4-difluorophenyl) cyclopropanaminium (2R)-2-hydroxy-2-phenylethanoate.

Step 1: Preparation of (E)-3-(3,4-difluorophenyl)-2-propenoic Acid

A stirred mixture of pyridine (15.5 kg) and piperidine (0.72 kg) were heated to 90° C. Malonic acid (17.6 kg) was added, followed by slow addition, over 50 minutes, of 3,4-difluorobenzaldehyde (12.0 kg). The reaction mixture was stirred at 90° C. for a further 4 hours and 36 minutes. Water (58.5 kg) was added and 32 litres of the pyridine/water mixture then was distilled out of the reactor under reduced pressure. The reaction mixture was acidified to pH 1 with 37% hydrochloric acid (6.4 kg) over a 40 minute period, then cooled to 25° C. with strong stirring. The solids were collected by filtration, washed twice with 1% hydrochloric acid (34.8 L per wash), once with water (61 L) and then deliquored thoroughly in the filter. The product was then dried under vacuum at 40° C. for 24 hours and 40 minutes, affording 13.7 kg of the crystalline product.

Step 2: Preparation of (E)-3-(3,4-difluorophenyl)-2-propenyl Chloride

A stirred mixture of (E)-3-(3,4-difluorophenyl)-2-propenoic acid (8.2 kg), toluene (7.4 kg) and pyridine (0.18 kg) was heated to 65° C. and then thionyl chloride (7.4 kg) was added over 30 minutes. The reaction was stirred for a further 2 h 15 minutes after the addition was complete, then diluted with toluene (8.7 kg). Excess thionyl chloride, sulfur dioxide and hydrogen chloride were then distilled out, together with toluene (10 L), under reduced pressure, yielding a solution of the (E)-3-(3,4-difluorophenyl)-2-propenoyl chloride (approximately 9 kg) in toluene.

Step 3: Preparation of (1R,2S,5R)-2-isopropyl-5-methylcyclohexyl (E)-3-(3,4-difluorophenyl)-2-propenoate A solution of L-menthol (7.1 kg) in toluene (8.5 kg) was added over a 20 minute period to the solution of (E)-3-(3,4-difluorophenyl)-2-propenoyl chloride (prepared as in Step 2) and pyridine (0.18 kg, 2.28 mol) stirring at 65° C. The reaction mixture was stirred at 65° C. for a further 4 hours and 40 minutes after the addition was complete, then cooled to 25° C. and stirred for a 14 hours. The solution was diluted with toluene (16 kg), washed with 5% aqueous sodium chloride (6.4 kg), then 6% sodium hydrogen carbonate (6.47 kg), then water (6.1 kg). The solution was dried azeotropically by distillation of the solvent (20 L) under reduced pressure. Dimethyl sulfoxide (33.9 kg) was added and the remaining toluene was distilled off under reduced pressure, affording 47.3 kg of a solution of (1R,2S,5R)-2-isopropyl-5-methylcyclohexyl (E)-3-(3,4-difluorophenyl)-2-propenoate (approx. 13.3 kg) in dimethyl sulfoxide.

Step 4: Preparation of Dimethylsulfoxonium Methylide (dimethyl(methylene)oxo-$\lambda^6$-sulfane Sodium hydroxide powder (1.2 kg), prepared by milling sodium hydroxide pellets in a rotary mill through a 1 mm metal sieve, and trimethylsulfoxonium iodide (6.2 kg) were stirred in dimethyl sulfoxide (25.2 kg) under a nitrogen atmosphere at 25° C. for 90 min. The solution was used directly in the preparation of (1R,2S,5R)-2-isopropyl-5-methylcyclohexyl trans-2-(3,4-difluorophenyl)cyclopropanecarboxylate.

Step 5: Preparation of (1R,2S,5R)-2-isopropyl-5-methylcyclohexyl Trans-2-(3,4-difluorophenyl)cyclopropanecarboxylate A solution of (1R-2S,5R)-2-isopropyl-5-methylcyclohexyl (E)-3-(3,4-difluorophenyl)-2-propenoate (approximately 8.6 kg) in dimethyl sulfoxide (approximately 27.9 kg) was added with stirring over 20 minutes to a mixture of dimethylsulfoxonium methylide (approximately 2.6 kg, prepared as described above), sodium iodide (approximately 4.2 kg), water (approximately 500 g) and sodium hydroxide (approximately 56 kg) in dimethylsulfoxide (27.7 kg) at 25° C. The reaction mixture was stirred for a further 2 hours and 50 minutes at 25° C., then used directly for the preparation of (1R,2S,5R)-2-isopropyl-5-methylcyclohexyl Trans-(1R, 2R)-2-(3,4-difluorophenyl)cyclopropanecarboxylate.

Step 6: Preparation of (1R,2S,5R)-2-isopropyl-5-methylcyclohexyl Trans-(1R,2R)-2-(3,4-difluorophenyl)cyclopropanecarboxylate A crude solution of (1R,2S,5R)-2-isopropyl-5-methylcyclohexyl trans-2-(3,4-difluorophenyl)cyclopropanecarboxylate produced as described in step 5 was heated with stirring from 25° C. to 50° C. over a 1 hour period and the temperature was maintained for a further hour. The mixture was then cooled with stirring from 50° C. to 35° C. over 4 hours, kept at 35° C. for 1 hour, then cooled to 26° C. over 4 hours, kept at 26° C. for 1 hour, then cooled to 19° C. over 3 hours and kept at 19° C. for 5 hours and 10 minutes. The product was collected by filtration, affording a crystalline solid (2.7 kg) which was shown to contain a mixture of (1R,2S,5R)-2-isopropyl-5-methylcyclohexyl trans-(1R,2R)-2-(3,4-difluorophenyl)cyclopropanecarboxylate (1.99 kg) and (1R,2S,5R)-2-isopropyl-5-methylcyclohexyl trans-(1S,2S)-2-(3,4-difluorophenyl)cyclopropanecarboxylate (85 g).

Step 7: Preparation of trans-(1R,2R)-2-(3,4-difluorophenyl)cyclopropanecarboxylic Acid (1R,2S,5R)-2-isopropyl-5-methylcyclohexyl trans-(1R,2R)-2-(3,4-difluorophenyl)-cyclopropanecarboxylate (9.6 kg, 91.8% diastereomeric excess) was dissolved in ethanol (13.8 kg) and heated with stirring to 46° C. 45% aqueous sodium hydroxide (3.1 kg) was added over a 20 minute period and the mixture was stirred for a further 2 hours and 27 minutes. Solvent (28 L) was distilled out of the mixture under reduced pressure, then the mixture was cooled to 24° C. and diluted with water (29.3 kg), after which the liberated menthol was extracted into toluene (3 washes of 3.3 kg each). The remaining aqueous material was acidified to pH 2 with 37% hydrochloric acid (3.3 L) and the product was extracted into toluene (8.6 kg, then 2 more washes of 4.2 kg and 4.31 kg). The combined toluene extracts were washed with 1% hydrochloric acid (4.9 L), then diluted with further toluene (4.2 kg) and azeotropically dried by distillation of the solvent (25 L) under reduced pressure. A final dilution with toluene (24.2 kg) was followed by distillation of the solvent under reduced pressure (10 L) affording a solution containing trans-(1R,2R)-2-(3,4-difluorophenyl)cyclopropanecarboxylic acid (approximately 3.45 kg) suitable for the production of trans-(1R,2R)-2-(3,4-difluorophenyl)cyclopropanecarbonyl chloride.

Step 8: Preparation of Trans-(1R,2R)-2-(3,4-difluorophenyl)cyclopropanecarbonyl Chloride Pyridine (70 ml) was added to a solution of trans-(1R,2R)-2-(3,4-difluorophenyl)cyclopropanecarboxylic acid (approximately 3.45 kg) in toluene (approximately 12-15 kg)), prepared as described above and the mixture was then heated to 65° C. Thionyl chloride (2.3 kg) was added over a period of 1 hour and the mixture was stirred at 70° C. for 3 hours. Thionyl chloride (0.5 kg) was added and the mixture was stirred a further 2 hours at 70° C. A final aliquot of thionyl chloride (0.5 kg) was added and the reaction mixture was stirred for 1 hour at 70° C., then cooled to 40° C. Periodic additions of toluene (45 kg, 3 additions of 15 kg each) were made during distillation of solvent (approximately 60 L) from the mixture under reduced pressure, then the solution of trans-(1R,2R)-2-(3,4-difluorophenyl)cyclopropanecarbonyl chloride (approximately 3.8 kg) in toluene (approximately 6-9 L) was cooled to 20° C.

Step 9: Preparation of trans-(1R,2R)-2-(3,4-difluorophenyl)cyclopropanecarbonyl Azide A solution of trans-(1R,2R)-2-(3,4-difluorophenyl)cyclopropanecarbonyl chloride (approximately 3.8 kg) in toluene (approximately 6-9 L), prepared in Step 8, at 1° C. was added over a period of 74 minutes to a mixture of sodium azide (1.24 kg), tetrabutylammonium bromide (56 g) and sodium carbonate (922 g) in water (6.2 kg), stirring at 1.5° C. The mixture was stirred at 0° C. for 1 hour and 55 minutes, then the aqueous layer was diluted with cold water (3.8 kg), stirred briefly, then separated. The toluene layer was washed once more at 0° C. with water (3.5 kg), then with 20% aqueous sodium chloride (3.8 L), then stored at 3° C. for further use.

Step 10: Preparation of Trans-(1R,2S)-2-(3,4-difluorophenyl)cyclopropylamine A cold solution of trans-(1R,2R)-2-(3,4-difluorophenyl) cyclopropanecarbonyl azide prepared as described in Step 9 was added over a period of 41 minutes to toluene (6.0 kg) stirring at 100° C. The mixture was stirred for a further 55 minutes at 100° C., then cooled to 20° C. and added over a period of 2 hours and 15 minutes to hydrochloric acid (3M, 18.2 kg) stirring at 80° C. After 65 minutes the solution was diluted with water (34 kg) and cooled to 25° C. The toluene layer was removed and the aqueous layer was basified to pH 12 with 45% aqueous sodium hydroxide (3.8 kg) and the product was then extracted into ethyl acetate (31 kg) and washed twice with water (13.7 kg per wash), affording a solution containing trans-(1R,2S)-2-(3,4-difluorophenyl)cyclopropylamine (2.6 kg, 91.8% enantiomeric excess) in ethyl acetate (29.5 L).

Step 11: Preparation of Trans-(1R,2S)-2-(3,4-difluorophenyl)cyclopropanaminium (2R)-2-hydroxy-2-phenylethanoate R-(−)-Mandelic acid (2.26 kg) was added to a solution containing trans-(1R,2S)-2-(3,4-difluorophenyl)cyclopropylamine (2.6 kg, 91.8% enantiomeric excess), stirring at 17° C. in ethyl acetate (45.3 L). The mixture was stirred at 25° C. for 3 hours and 8 minutes, then filtered and washed twice with ethyl acetate (13.8 kg total) The crystalline product was dried at 40° C. under reduced pressure for 23 hours, affording trans-(1R,2S)-2-(3,4-difluorophenyl)-cyclopropanaminium (2R)-2-hydroxy-2-phenylethanoate (4.45 kg).

EXAMPLE 3

This Example illustrates the preparation of 4,6-dichloro-2-(propylsulfanyl)-5-pyrimidinamine.

Step 1: 4,6-Dihydroxy-2-(propylsulfanyl)pyrimidine

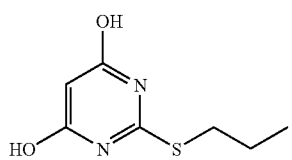

Water (670 ml) was added to 2-thiobarbituric acid (200 g). The resulting mixture was stirred and sodium hydroxide (126.3 g) was added in portions. The mixture was stirred for 40 min. then diluted with water. 1-Methyl-2-pyrrolidinone (400 ml) and 1-iodopropane (140.9 ml) were then added. The resulting slurry was stirred at 20° C. for 22 h. The pH of the mixture was then adjusted to 6.5 by addition of 1M HCl (600 ml) over 30 min, then to pH 2.5 by the addition of 6 M HCl (180 ml) over a further 30 min. The resulting slurry was stirred for 18 h and the product was isolated by filtration and washed successively with water (4×100 ml), ethanol (200 mm) and water (2×200 ml). The product was dried under reduced pressure overnight at 50° C. to yield the title product as a white powder (185 g).

Step 2: 4,6-Dihydroxy-5-[(E)-2-(4-methylphenyl)diazerryl]-2-(propylsulfanyl)pyrimidine

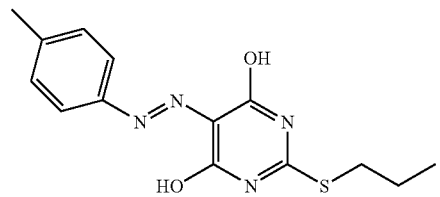

Ethanol (25 ml), 4,6-dihydroxy-2-(propylsulfanyl)pyrimidine (Step 1; 5 g) and water (25 ml) were stirred together at room temperature. Sodium hydroxide (1.02 g) was added and a clear solution obtained. The resulting solution was cooled to 0° C. and then sodium acetate (9.42 g) was added to give Solution A.

In a separate vessel, a solution of p-toluidine (3.01 g) in water (10 ml) was prepared. To this was added concentrated hydrochloric acid (37% w/w aqueous solution; 8.45 ml). The resulting mixture was cooled to 0° C., and a solution of sodium nitrite (2.16 g) in water (10 ml) was cooled to 0° C. and added dropwise to the toluidine—containing reaction mixture over 30 minutes. The temperature during the addition was kept between 0 and 5° C. The resulting mixture was cooled to 0° C. and added to the cold (0° C.) Solution A (the temperature rose to 8° C.). The resulting yellow suspension was stirred overnight and the pH of the mixture was adjusted to pH 1 by addition of 6 M HCl. The mixture was filtered and the collected product washed with water (25 ml) ethanol (10 ml). The product was dried under reduced pressure at 50° C. over 24 h to give the product as a yellow solid (6.97 g).

Step 3: 4,6-Dichloro-5-[(E)-2-(4-methylphenyl)diazenyl]-2-(propylsulfanyl)pyrimidine

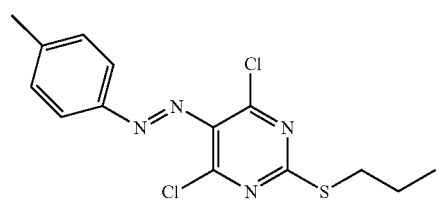

Pyridine (2.58 ml) was added to a stirred, heated (70° C.) slurry of 4,6-dihydroxy-5-[(E)-2-(4-methylphenyl)diazenyl]-2-(propylsulfanyl)pyrimidine (Step 2, 5 g) in toluene (15 ml). Phosphorous oxychloride (18.7 ml) was added dropwise to the mixture over 15 min (exotherm to 94° C.). The reaction mixture was heated for a further 4.5 h then evaporated. The residue was azeotroped twice with toluene (2×30 ml). The residue was dissolved in toluene (50 ml) and filtered to remove some solids. The collected solid was washed with toluene and the combined filtrates washed with water (30 ml) and saturated aqueous sodium bicarbonate solution (30 ml). Evaporation gave the title product (4.98 g) as a red oil that slowly crystallised on standing.

Step 4: Preparation of
4,6-dichloro-2-(propylsulfanyl)-5-pyrimidinamine

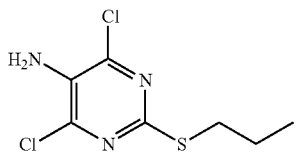

A stirred solution of 4,6-dichloro-5-[(E)-2-(4-methylphenyl)diazenyl]-2-(propylsulfanyl)pyrimidine (Step (3), 1.1 kg) in 2-propanol (16.6 kg) was hydrogenated for 1 h at 40° C./3.2 bar over a platinum on carbon catalyst (0.81 kg, 50% w/w Pt/C). The hydrogen gas pressure was released and the reactor flushed with nitrogen. The reaction mixture was filtered. The collected solid was washed with 2-propanol (1.7 kg) and the combined filtrates were concentrated under reduced pressure. The residual oil was cooled to 20° C. and dissolved in ethyl acetate (5 kg) and water (5.51) was added. The pH of the stirred mixture was adjusted to pH 2 by the addition of 3M aqueous hydrochloric acid (800 ml). The phases were allowed to separate and the aqueous phase was discharged. Water (2.751) was added to the organic phase and the pH was adjusted to 2 by the addition of a small amount of 3M HCl (45 ml). The aqueous phase was separated and the organic phase concentrated under reduced pressure at 30-50° C., to give 4,6-dichloro-2-(propylsulfanyl)-5-pyrimidinamine as a reddish viscous oil containing ethyl acetate that was dissolved in ethanol (8.5 kg). Solvent (6.51 of ethanol/ethyl acetate) was then removed by distillation at reduced pressure. A further portion of ethanol (4.5 kg) leas added to the residue and the distillation repeated to remove 6.5 l of solvent. The ethanol solution of the product was used without further purification in the following step.

EXAMPLE 4

This Example illustrates the preparation of [1S-[1α, 2α, 3β(1S*,2R*), 5β]]-3-[7-[2-(3,4-difluorophenyl)cyclopropyl-amino]-(propylthio)-3H-1,2,3-triazolo[4,5-d]pyrimidin-3-yl]-5-(2-hydroxyethoxy)cyclopentane-1,2-diol (alternatively names (1S,2S,3R,5S)-3-[7-{[(1R,2S)-2-(3,4-difluorophenyl)cyclopropyl]amino}-5-(propylsulfanyl)-3H-[1,2,3]triazolo[4,5-d]pyrimidin-3-yl]-5-(2-hydroxyethoxy)-1,2-cyclopentanediol).

Step 1: Preparation of [3aR-(3aα,4α,6α,6aα)]-2-[[6-[[5-amino-6-chloro-2-(propylthio)-4-pyrimidinyl]amino]tetrahydro-2,2-dimethyl-3aH-cyclopenta[d][1,3]dioxol-4-yl]oxy]ethanol (Alternatively Named 2-[((3aR,4S,6R,6aS)-6-{[5-amino-6-chloro-2-(propylsulfanyl)-4-pyrimidinyl]amino}-2,2-dimethyltetrahydro-3aH-cyclopenta[d][1,3]dioxol-4-yl)oxy]-1-ethanol

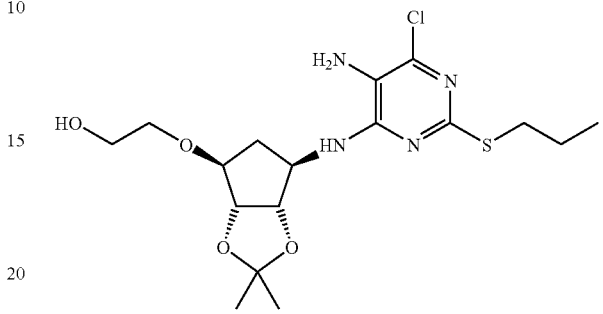

The ethanolic solution of 4,6-dichloro-2-(propylsulfanyl)-5-pyrimidinamine, (prepared as in Example 3, Step 4) was added to 2-{[(3aR,4S,6R,6as)-6-amino-2,2-dimethyltetrahydro-3aH-cyclopenta[d][1,3]-dioxol-4-yl]oxy}-1-ethanol, L-tartaric acid salt (1:1) (1.18 kg). To the resulting stirred thick slurry was charged triethylamine (0.95 kg) maintaining the temperature between 20 and 25° C. The reactor was sealed and the temperature increased to 120-125° C. The reaction mixture was kept within this temperature range for 30 h, then cooled to 75° C., and the pressure release. The temperature of the mixture was adjusted to 50° C. and the solvent distilled off under reduced pressure at 30 to 40° C. Ethyl acetate (4.95 kg) and water (5.51) were added, the pH of the mixture adjusted to pH 5 by the addition of 3M hydrochloric acid (100 ml), and the phases were separated. The organic-phase was washed with 15% w/w brine (5.51), then separated. The organic phase was concentrated under reduced pressure (4.81 of solvent removed) to give 2-[((3aR,4S,6R,6aS)-6-{[=-amino-6-chloro-2-(propylsulfanyl)-4-pyrimidinyl]amino}-2,2-dimethyltetrahydro-3aH-cyclopenta[d][1,3]dioxo-4-yl)oxy]-1-ethanol as a brown-red viscous oil containing ethyl acetate. The product is used without further purification in the following step.

Step 2: Preparation of [3aR-(3aα,4α,6α,6aα)]-2-[[6-[7-chloro-5-(propylthio)-3H-[1,2,3]triazolo[4,5-d]pyrimidin-3-yl]tetrahydro-2,2-dimethyl-3aH-cyclopenta[d][1,3]dioxol-4-yl]oxy]ethanol
(Alternatively Named 2-({(3aR,4S,6R,6 as)-6-[7-chloro-5-(propylsulfanyl)-3H-[1,2,3]triazolo[4,5-d]pyrimidin-3-yl]-2,2-dimethyltetrahydro-3aH-cyclopenta-[d][1,3]dioxol-4-yl}oxy)-1-ethanol).

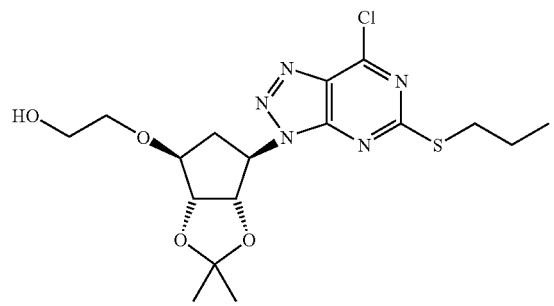

2-[((3aR,4S,6R,6aS)-6-{[5-Amino-6-chloro-2-(propyl-sulfanyl)-4-pyrimidinyl]amino}-2,2-dimethyltetrahydro-3aH-cyclopenta[d][1,3]dioxol-4-yl)oxy]-1-ethanol, as obtained in Step 1 was dissolved in acetic acid (5.75 kg) and water (650 ml). The resulting solution was cooled to 2° C. (with stirring) and a solution of sodium nitrite (232 g) in water (1.251) was added such that the mixture temperature was held below 7° C. The mixture was then allowed to warm to 7° C. then ethyl acetate (8.9 kg) was added. Aqueous potassium carbonate solution (41, 37% w/w) was added. The mixture was separated and the organic phase washed with further aqueous potassium carbonate solution (3.8 kg, 21% w/w). The aqueous phase was discarded and the organic phase concentrated under reduced pressure to give the sub-titled compound as a red-brown viscous oil used without further purification in the following step.

Step 3: Preparation of {3aR-[3aα,4α,6α(1R*,2S*),6aα]}-2-[6-({7-[2-(3,4-difluorophenyl) cyclopropyl]amino-5-(propylthio)-3H-1,2,3-triazolo[4,5-d]pyrimidin-3-yl}tetrahydro-2,2-dimethyl-4H-cyclopenta-1,3-dioxol-4-yl)oxy]ethanol (alternatively named 2-({(3aR,4S,6R,6aS)-6-[7-{[(1R,2S)-2-(3,4-difluorophenyl)-cyclopropyl]amino}-5-(propylsulfanyl)-3H-[1,2,3]triazolo[4,5-d]pyrimidin-3-yl]-2,2-dimethyltetrahydro-3aH-cyclopenta[d][1,3]dioxol-4-yl}oxy)-1-ethanol)

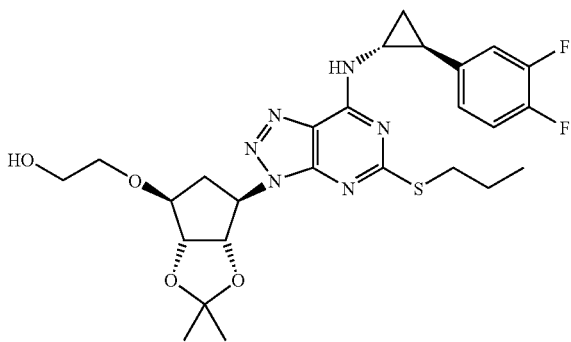

trans-(1R,2S)-2-(3,4-Difluorophenyl)cyclopropan-aminium (2R)-2-hydroxy-2-phenylethanoate (0.77 kg) was charged to a vessel followed by a solution of 2({(3aR,4S,6R,6aS)-6-[7-chloro-5-(propylsulfanyl)-3H-[1,2,3]triazolo [4,5-d]pyrimidin-3-yl]-2,2-dimethyltetrahydro-3aH-cyclopenta-[d][1,3]dioxol-4-yl}oxy)-1-ethanol (prepared as in Step 2) dissolved in acetonitrile (3.85 kg). To the resulting stirred mixture was added triethylamine (0.81 kg) at such a rate that the reaction temperature was maintained between 20-25° C. The reaction mixture was stirred for 13 h then concentrated at reduced pressure at 30° C. To the residue was added ethyl acetate (8.1 kg) and water (4.61). The pH of the stirred two phase mixture was adjusted to pH 4 by the addition of 3M HCl (450 ml). The mixture was then allowed to settle and separate. The aqueous phase was separated and the retained organic phase was washed with 15% w/w aqueous sodium chloride solution (4.15 kg), the organic phase was concentrated under reduced pressure at 30-50° C. giving the crude title compound as a red oil, that was used directly in the next step.

Step 4: Preparation of [1S-[1α,2α,3β(1S*,2R*),5β]]-3-[7-[2-3,4-difluorophenyl)-cyclopropy-lamino]-5-(propylthio)-3H-1,2,3-triazolo[4,5d]-pyrimidin-3-yl]-5-(2-hydroxyethoxy)cyclopentane-1,2-diol (alternatively named (1S,2S,3R,5S)-3-[7-{[(1R,2S)-2-(3,4-Difluorophenyl)cyclopropyl]amino}-5-(propylsulfanyl)-3H-[1,2,3]triazolo[4,5-d]pyrimidin-3-yl]-5-(2-hydroxyethoxy)-1,2-cyclopentanediol)

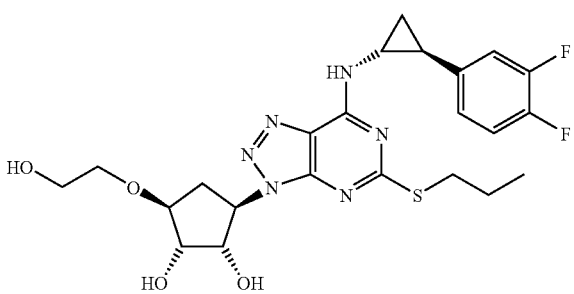

Aqueous hydrochloric acid (3 M, 4.81), was added to a stirred solution of 2-({(3aR,4S,6R,6aS)-6-[7-{[(1R,2S)-2-(3,4-difluorophenyl)cyclopropyl]-amino}-5-(propylsulfa-nyl)-3H-[1,3]triazolo[4,5-d]pyrimidin-3-yl]-2,2-dimethyltetrahydro-3aH-cyclopenta[d][1,3]dioxol-4-yl}oxy)-1-ethanol (1.931 kg) in methanol (13.4 kg), maintaining the temperature during the addition between 20 and 25° C. The mixture was then stirred for 24 h at 20° C. Sodium hydroxide (45% w/w aqueous solution; 780 ml) was then added to adjust the pH of the mixture to pH 7.2. The methanol was then removed by distillation at reduced pressure and ethyl acetate (14.3 kg) added. The mixture was heated to 45° and the aqueous layer separated. The organic phase was then washed 15% w/w aqueous sodium chloride solution (7.2 kg). Ethyl acetate (101) was removed by distillation at reduced pressure. Fresh ethyl acetate (7.2 kg) was charged and the mixture filtered. The filter was washed with ethyl acetate (1.5 kg). The combined filtartes were dried by repeated addition/distillation of ethyl acetate. When the solution was dry, the product content of the ethyl acetate solution was determined by a chromatographic assay technique and found to contain 1016 g of product, the concentration of the ethyl acetate was adjusted until a concentration of 5 ml ethyl acetate/g of the crude product was reached. The ethyl acetate solution was heated to 47° C. and isooctane (2.5 ml/g product, 2540 ml) was then added over 15 min. The resulting slurry was stirred for 30 min. then more iso-octane (2540 ml) was added over 5 mins. The resulting mixture was stirred at 48-50° C. for 30 min then cooled to 20° C. over 3 h. The slurry was stirred at 20° C. for 6.5 h then filtered and washed with a mixture consisting of iso-octane (1.25 kg) and ethyl acetate (1.6 kg). The collected solid was dried in vacuo to give the title compound (920 g).

If desired, the crude product can be further purified by employing one of the following three methods.

Recrystallization from Ethyl Acetate/Iso-octane

The crude product is dissolved in ethyl acetate (4.8 ml/g) at 55° C., then filtered to remove particles. The clear solution is taken back to the reactor for recrystallisation and the temperature is set at 50° C. iso-Octane is then added (4.8 ml/g) during 10 min. The slurry is allowed to stand for 30 minutes after which it is cooled to 20° C. during 2-3 hours and finally the temperature is kept at 20° C. for about 30 minutes. The product is then filtered and washed with iso-octane (2×1.5 ml/g). The product is dried under reduced pressure at 50° C. giving pure product (>98% pure by h.p.l.c. analysis).

Slurry with N-butyl Acetate

The crude product is suspended in n-butyl acetate 4 ml/g and stirred at room temperature for 10 hours. The slurry is cooled to 0° C. during 3-4 hours and kept at 0° C. for 1 hour. The product is filtered and washed with 2 ml/g of cold n-butyl acetate (<0° C.). The product is then dried in vacuo at 50° C., giving pure product (>98% pure by h.p.l.c. analysis).

Slurry with Iso-propanol

The crude product is suspended in iso-propanol 3 ml/g and stirred at 50° C. for 72 h. The slurry is then cooled to 20° C. during 3 hours and the temperature is kept at 20° C. for about 30 minutes. The product is then filtered and washed with 1 ml/g of cold iso-propanol (<0° C.). Finally, the product is dried under reduced pressure at 50° C. giving pure product (>98% pure by h.p.l.c. analysis).

The invention claimed is:

1. A process for preparing a salt of a compound of formula (III):

(III)

comprising reacting a compound of formula (III) with a mineral or organic acid.

2. A process for preparing a salt of a compound of formula (III):

(III)

comprising the steps:
(a) preparing a compound of formula (XI):

(XI)

by reacting a compound of formula (XII):

(XII)

with benzyl chloroformate;
(b) preparing a compound of formula (X):

(X)

by reacting a compound of formula (XI) with a compound L-CH$_2$CO$_2$R* {wherein R* is C$_{1-4}$ alkyl; and L is a leaving group};
(c) preparing a compound of formula (IX):

(IX)

by reducing a compound of formula (X);
(d) preparing a compound of formula (III):

(III)

by deprotecting a compound of formula (IX); and,
(e) preparing a salt of a compound of formula (III) by reacting the compound of formula (III) with a mineral or organic acid.

3. A salt of a compound of formula (III).

* * * * *